(12) United States Patent
Brahm

(10) Patent No.: US 11,547,731 B2
(45) Date of Patent: *Jan. 10, 2023

(54) METHODS FOR THE TREATMENT OF INFLAMMATION AND PAIN USING HUMAN BIRTH TISSUE MATERIAL COMPOSITION

(71) Applicant: Brahm Holdings, LLC, Germantown, TN (US)

(72) Inventor: Timothy R. Brahm, Germantown, TN (US)

(73) Assignee: BRAHM HOLDINGS, LLC, Germantown, TN (US)

(*) Notice: Subject to any disclaimer, the term of this patent is extended or adjusted under 35 U.S.C. 154(b) by 56 days.

This patent is subject to a terminal disclaimer.

(21) Appl. No.: 16/026,569

(22) Filed: Jul. 3, 2018

(65) Prior Publication Data

US 2018/0311285 A1 Nov. 1, 2018

Related U.S. Application Data

(63) Continuation of application No. 14/203,658, filed on Mar. 11, 2014, now Pat. No. 10,039,792.

(60) Provisional application No. 61/802,413, filed on Mar. 16, 2013.

(51) Int. Cl.
*A61K 35/50* (2015.01)

(52) U.S. Cl.
CPC ..................... *A61K 35/50* (2013.01)

(58) Field of Classification Search
CPC ....................................................... A61K 35/50
See application file for complete search history.

(56) References Cited

U.S. PATENT DOCUMENTS

| | | | |
|---|---|---|---|
| 3,409,016 A | 11/1968 | Foley | |
| 5,036,056 A | 7/1991 | Kludas | |
| 6,152,142 A | 11/2000 | Tseng | |
| 6,326,019 B1 | 12/2001 | Tseng | |
| 7,132,452 B2 | 11/2006 | Lee et al. | |
| 7,268,163 B2 | 9/2007 | Konowalchuk et al. | |
| 7,682,623 B2 | 3/2010 | Eini et al. | |
| 7,727,550 B2 | 6/2010 | Siegal et al. | |
| 7,871,646 B2 | 1/2011 | Ghinelli | |
| 8,071,135 B2 | 12/2011 | Liu et al. | |
| 8,105,590 B2 | 1/2012 | Yao et al. | |
| 8,153,162 B2 | 4/2012 | Tseng et al. | |
| 8,182,840 B2 | 5/2012 | Tseng et al. | |
| 8,182,841 B2 | 5/2012 | Tseng et al. | |
| 8,187,639 B2 | 5/2012 | Tseng et al. | |
| 8,221,741 B2 | 7/2012 | Marshall et al. | |
| 8,455,009 B2 | 6/2013 | Tseng et al. | |
| 8,460,650 B2 | 6/2013 | Edinger et al. | |
| 8,956,862 B2 | 2/2015 | Pal et al. | |
| 2004/0057938 A1* | 3/2004 | Ghinelli | A61K 35/48 424/93.7 |
| 2007/0021762 A1 | 1/2007 | Liu et al. | |
| 2007/0031471 A1 | 2/2007 | Peyman | |
| 2007/0275441 A1 | 11/2007 | Jessup et al. | |
| 2007/0292401 A1 | 12/2007 | Harmon et al. | |
| 2008/0286378 A1 | 11/2008 | Behrens | |
| 2010/0159025 A1* | 6/2010 | Kramer | A61P 29/00 424/583 |
| 2012/0141595 A1 | 6/2012 | Tseng et al. | |
| 2012/0328583 A1 | 12/2012 | Herzberg et al. | |
| 2013/0004465 A1* | 1/2013 | Aberman | A61P 3/00 424/93.7 |
| 2013/0287741 A1 | 10/2013 | Stilwell et al. | |
| 2014/0037598 A1 | 2/2014 | Jansen et al. | |
| 2014/0050788 A1 | 2/2014 | Daniel et al. | |
| 2014/0052247 A1 | 2/2014 | Daniel et al. | |

FOREIGN PATENT DOCUMENTS

| | | | |
|---|---|---|---|
| CN | 1235026 | 11/1999 | |
| EP | 0 285 370 | 10/1988 | |
| EP | 2 536 417 | 12/2012 | |
| WO | WO-2006/094247 | 1/2006 | |
| WO | WO-2009/052132 | 1/2009 | |
| WO | WO-2012/003377 | 1/2012 | |
| WO | WO-2012112410 A2 * | 8/2012 | ............. A61K 35/50 |

OTHER PUBLICATIONS

Morrison "Bacterial Joint Inflammation". Update: Sep. 28, 2018. Retrieved from the Internet on: Sep. 28, 2021.. Retrieved from: <URL: https://www.healthline.com/health/bacterial-joint-inflammation>. (Year: 2018).*
American Academy of Allergy Asthma and Immunology. "Immunosuppressive Medication for the Treatment of Autoimmune Disease". Retrieved from the Internet on: Sep. 28, 2021. Retrieved from: <URL: https://www.aaaai.org/Conditions-Treatments/Related-Conditions/immunosuppressive>. (Year: 2021).*
CDC. "Chikungunya virus". Internet Update Date: Oct. 17, 2018. Retrieved from the Internet on: Sep. 28, 2021. Retrieved from: <URL: https://www.cdc.gov/chikungunya/symptoms/index.html>. (Year: 2018).*
"Plasma-Lyte A" from Baxter Healthcare Corporation, Internet Date: Dec. 2009, retrieved on Mar. 20, 2017 (https://dailymed.nlm.nih.gov/dailymed/archives/fdaDrug Info.cfm?archiveid= 14376).
Drug information for "Plasma-Lyte A" obtained from Drugs.com on Dec. 8, 2016 (https://www.drugs.com/pro/plasma-lyte-a.html), pp. 1-11.
http://www.pharmacygeoff.md/Placentrex_Gel_Nitrogen_Fresh_Human_Placental_Extract_025_p_1657.html, accessed Feb. 12, 2016.
http://www.placentrex.com/injection.html, accessed Feb. 12, 2016.

(Continued)

*Primary Examiner* — Amy L Clark
(74) *Attorney, Agent, or Firm* — Barnes & Thornburg, LLP

(57) ABSTRACT

Methods of treating inflammation, pain or both inflammation and pain in a subject are provided. The method includes the step of administering a human birth tissue material composition on or within an affected site of a body. The methods are particularly suitable for treatment of inflammation, pain or both inflammation and pain arising from a viral infection.

8 Claims, 3 Drawing Sheets

(56) References Cited

OTHER PUBLICATIONS

Avanzi et al., "Susceptibility of Human Placenta Derived Mesenchymal Stromal/Stem Cells to Human Herpesviruses Infection," PLOS One, vol. 8, Iss. 8, pp. 1-14, 2013.

Brooke et al., "Manufacturing of human placenta-derived mesenchymal stem cells for clinical trials," British Journal of Haematology, vol. 144, pp. 571-579, 2008.

Fuller et al., "Stem Cells," Clinical Applications of Cryobiology, pp. 127-134, 2000.

Gavin, "Histopathology of fresh human aortic valve allografts," Thorax, vol. 28, pp. 482-487, 1973.

Haimov-Kochman et al. "Modification of the standard trizol-based technique improves the integrity of RNA isolated from Rnase-rich placental tissue," Clinical Chemistry, vol. 52, No. 1, pp. 159-160, 2006.

Heiligenhaus et al., British Journal of Ophthalmology, vol. 87, pp. 1215-1219, 2003.

Kagan, The Skin Bank, Chapter 15, in Total Burn Care, pp. 199-208, 2012.

Kaushal et al., International Journal of Tissue Reactions, vol. 23, No. 3, pp. 105-110, PubMed Abstract, 2001.

Parolini et al., "Concise Review: Isolation and Characterization of Cells from Human Term Placenta: Outcome of the First International Workshop on Placenta Derived Stem Cells," Stem Cells, vol. 26, pp. 300-311, 2008.

Sabapathy et al., "Long-Term Cultured Human Term Placenta-Derived Mesenchymal Stem Cells of Maternal Origin Displays Plasticity," Stem Cells International, vol. 2012, pp. 1-11, 2012.

Sheha et al., Cornea, vol. 28, No. 10, pp. 1118-1123, 2009.

\* cited by examiner

| | BATCH VOLUME AND ALIQUOT FILL CALCULATION | | | | | |
|---|---|---|---|---|---|---|
| A. | AMNION WEIGHT (AW) | | | | | |
| | | | | Amnion Weight (g) | (AW) _____ g | |
| B. | AMNION ALLOWABLE ALIQUOTS (AA) | | | | | |
| | (AW) _____ g    /    0.03 g    = Amnion Weight(g)      Minimum Amnion(g) per 1mL aliquot | | | | (AA) _____ | |
| C. | CELL COUNT | | | | | |
| | Amniotic Fluid Volume (mL) (A) | Total Cells Counted (5 Large Squares) (B) | Average Cells / Square (C) (C = B / 5) | Dilution Factor (D) | Total Cell Density (E) (Cells/mL) (E = C x D x $10^4$) | Total Cells (TC) (TC = E x A) |
| | (A) | (B) | (C) | (D) | (E) | (TC) |
| D. | ALIQUOT CELL DENSITY (ALIQUOT = 1 mL) | | | | | |
| | (TC) _____    /    (AA) _____    =     Total Cells         Amnion Allowable Aliquot | | | | (CD) _____ ml Aliquot Cell Density | |
| E. | BULK PRODUCT VOLUME (BV) | | | | | |
| | (AA) _____ = (BV) _____ | | | | | |
| F. | LOT VIAL FILL CALCULATIONS | | | | | |
| | Bulk Product Volume    (BV) | | = | | | mL |
| | Actual Vial Target 0.25 mL = | | X 0.25 = | | | mL |
| | Actual Vial Target 0.50 mL = | | X 0.50 = | | | mL |
| | Actual Vial Target 1.25 mL = | | X 1.25 = | | | mL |
| | TOTAL VIAL Target | | Total Vial Fill Volume* | | | mL |
| | * Total Vial Fill Volume Must be ≤ Bulk Product Volume | | | | | |

FIG. 2

| | SOLUTION CALCULATIONS | | |
|---|---|---|---|
| | SUSPENSION SOLUTIONS (SS) CALCULATIONS | | |
| a) | (BV) _____ mL = (SS) _____ mL<br>Bulk Product Volume (mL)　　　　Total Suspension Solution Volume (mL) | | |
| i) | Cell Suspension Solution (CS) | | |
| | _____ (SS) / 2 = | | _____ mL (CS) |
| | Component Description | Volume Calculation | Volume Required |
| | Plasma Lyte-A Injection (pH 7.4) | (CS) x 0.91 = | mL |
| | Human Albumin 25% Solution | (CS) x 0.09 = | mL |
| ii) | Amnion Suspension Solution (AS) | | |
| | _____ (SS) / 2 = | | _____ mL (AS) |
| | Component Description | Volume Calculation | Volume Required |
| | Plasma Lyte-A Injection (pH 7.4) | (AS) x 0.44 = | mL |
| | Human Albumin 25% Solution | (AS) x 0.36 = | mL |
| | DMSO (Dimethyl Sulfoxide), USP | (AS) x 0.20 = | mL |
| b) | AMNION CONTROL RATE FREEZE SOLUTION = 50 mL | | |
| | Component Description | Volume Calculation | Volume Required |
| | Plasma Lyte-A Injection (pH 7.4) | 50 ml x 0.44 = | 22 mL |
| | Human Albumin 25% Solution | 50 ml x 0.36 = | 18 mL |
| | DMSO (Dimethyl Sulfoxide), USP | 50 ml x 0.20 = | 10 mL |

FIG. 3

METHODS FOR THE TREATMENT OF INFLAMMATION AND PAIN USING HUMAN BIRTH TISSUE MATERIAL COMPOSITION

CROSS-REFERENCE TO RELATED APPLICATIONS

This application is a continuation of U.S. application Ser. No. 14/203,658, filed Mar. 11, 2014, which claims priority to U.S. Provisional Application No. 61/802,413 filed Mar. 16, 2013, the contents of which is incorporated herein in its entirety.

FIELD OF THE INVENTION

Methods for treating or otherwise managing inflammation and/or pain by administering a human birth tissue material composition are provided.

BACKGROUND OF THE INVENTION

Neurogenic inflammation can be triggered by activation of nociceptive and thermal-sensitive nerve endings in tissues. Such activation can be caused by tissue injury, viral infection, or innate conditions, such as autoimmune disease. For example, once an individual has been infected with the herpes virus, the virus will thereafter remain latent in the body. In the latent state, the virus can settle in nerve cell bodies in the ganglia. Stimuli, such as influenza infection, other respiratory disorders, gastrointestinal infections, stress, fatigue, menstruation, pregnancy, allergy, sunlight, or fever, can activate the latent virus, which may then travel from the ganglia to the skin surface and multiply, causing various symptoms. Exemplary symptoms include pain, neurogenic inflammation, blistering, and other somatosensory system manifestations such as, for example, pain, itch, tickle, tingle, and numbness.

At the onset of such symptoms, conventional methods for the treatment of pain and inflammation are often initiated, for example, non-steroidal anti-inflammatory drugs (NSAIDs), antidepressants, and antiviral medications (e.g., acyclovir, famciclovir, or valacyclovir). Such conventional methods often fall short of true treatment by only providing temporary relief, masking symptoms and/or causing serious side effects from prolonged use. Thus, there remains a need for a safe and effective treatment of inflammation and pain which can be used without the side effects associated with long-term use of conventional treatments.

SUMMARY OF THE INVENTION

According to one aspect, a method of treating inflammation, pain or both inflammation and pain in a subject in need of treatment is provided. The method includes the step of administering an effective amount of a human birth tissue material composition on or within an affected site of a body. The affected site can be infected with at least one virus. The virus can be a member of the Herpesviridae family. Members of the Herpesviridae family include herpes simplex virus-1, herpes simplex virus-2, varicella zoster, herpes zoster, Epstein-Barr virus, cytomegalovirus, roseolovirus, pityriasis rosea, Kaposi's sarcoma-associated herpesvirus, or a combination thereof. The virus can be a member of the Poxviridae family, which can include Molluscum contagiosum virus.

According to another embodiment, the affected site can be neuronal tissue. According to another embodiment, the affected site can be skin or mucosal membrane. In such an embodiment, the skin or mucosal membrane may display a blister or lesion. According to one embodiment, the step of administering the human birth tissue material composition includes injecting the composition into the affected site. According to another embodiment, the step of administering the human birth tissue material composition includes topical administration to the affected site. According to one embodiment, the birth tissue material composition includes one or more of the components of the placental organ. The one or more of the components of the placental organ can include the placental globe, the umbilical cord, the umbilical cord blood, the chorionic membrane, the amniotic membrane, the Wharton's jelly, other gelatins, cells, and extracellular material or the amniotic fluid.

BRIEF DESCRIPTION OF THE DRAWINGS

FIG. 2 provides a batch volume and fill calculation sheet according to one embodiment; and FIG. 3 provides a solution calculation sheet according to one embodiment.

DETAILED DESCRIPTION OF THE INVENTION

Figure 1:
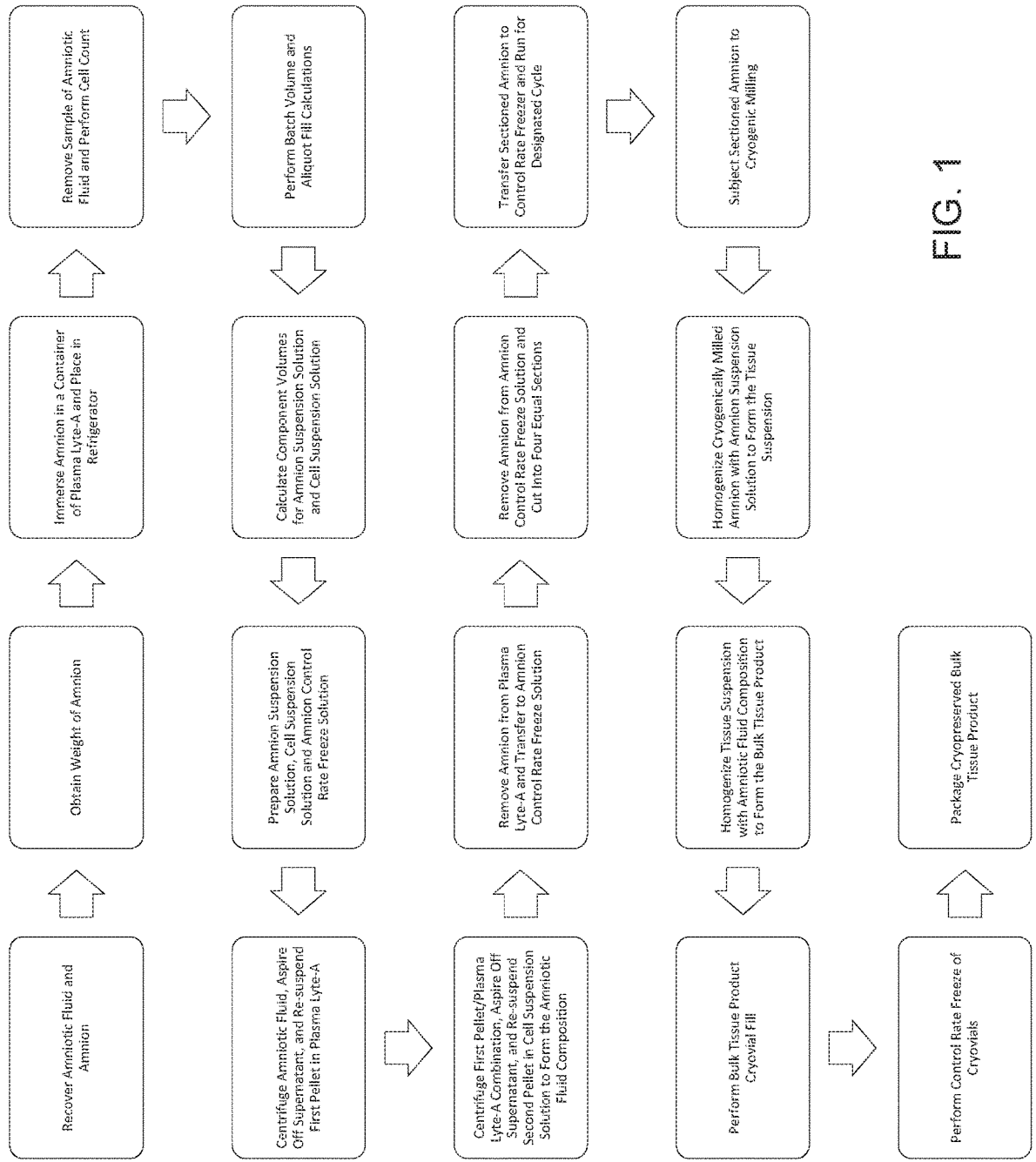
FIG. 1 is a schematic providing an overview of the method of preparing a human birth tissue material composition according to one embodiment.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, "human birth tissue material" encompasses one or more of the components of the placental organ including, but not limited to, the placental globe, the umbilical cord, the umbilical cord blood, the chorionic membrane, the amniotic membrane, the Wharton's jelly, other gelatins, cells, and extracellular material, and the amniotic fluid.

As used herein, "placental tissue components" encompasses one or more of the tissue components of the placental organ including, but not limited to, the placental globe, the umbilical cord, the umbilical cord blood, the chorionic membrane, the amniotic membrane, the Wharton's jelly and other gelatins, cells and extracellular material.

As used herein, the term "amnion" and "amniotic membrane" are used interchangeably.

As used herein, the term "effective amount" or "therapeutically effective amount" refer to an amount of the human birth tissue material composition sufficient to elicit the desired pharmacological or therapeutic effects, thus resulting in an effective treatment of a disease, condition, disorder, or the inflammatory or pain symptoms associated therewith.

As used herein, the term "treatment" or "treating" refers to the inhibition, reduction, delay or prevention of the onset or progression of the disease, condition, or disorder itself, as well as the delay or prevention of the onset or progression of symptoms (e.g., pain, inflammation) associated with the disease, condition, or disorder. Treatment may also be manifested by a decrease or elimination of symptoms, reversal of the progression of the disorder, as well as any other contribution to the well-being of the patient. The effective amount can vary, depending upon factors such as the condition of the patient, the severity of the symptoms of the disorder, and the manner in which the human birth tissue material is administered.

As used herein, the term "treatment of pain" and the like refers to complete elimination of pain; noticeable reduction of pain by the subject suffering pain; detectable reduction of pain or indicia of pain by objective criteria (e.g., heart rate, blood pressure, muscle tone); or a combination thereof.

As used herein, the term "mucosal membrane" refers to the mucosa of the nose, mouth, eye, ear, vagina or rectum.

A method of treating inflammation, pain, or both inflammation and pain in a subject is provided. The method includes the step of administering a human birth tissue material composition on or within an affected site of a body. The inflammation and/or pain may arise as a symptom(s) from an underlying disorder, disease, or condition. In certain embodiments, the site of pain can be a symptomatic manifestation of an underlying inflamed site on or within the body.

The birth tissue material composition administered in the methods of the present invention may be prepared as provided herein. One embodiment of a method of preparing a birth tissue material composition is provided in the schematic of FIG. 1. The method of preparing a human birth tissue material composition includes the step of recovering placental tissue components and amniotic fluid from a seronegative, healthy human. Potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-I I); and syphilis (a non-treponemal or treponemal-specific assay may be performed).

Human birth tissue is preferably recovered from a full-term Cesarean delivery of a newborn. Alternatively, human birth tissue is recovered from a full-term vaginal delivery of a newborn. The subsequent steps of preparing the human birth tissue material are performed in a controlled environment (i.e., certified biological safety cabinet, hood or clean room). Instruments, solutions, and supplies coming into contact with the human birth tissue material during processing are sterile. All surfaces coming in contact with the human birth tissue material intended for transplant are either sterile or draped using aseptic technique.

Once recovered, one or more of the placental tissue components can be removed via a sterile saline solution rinse, blunt dissection, scalpel, or a combination thereof, if necessary. According to one embodiment, the placental globe, umbilical cord, chorionic membrane, and other gelatins, fluids, cells and extracellular matrix are removed and discarded, leaving the amniotic membrane for further processing. In a preferred embodiment, the human birth tissue material is subject to the method of preparation described herein no more than four hours after recovery to preserve cell viability.

The retained placental tissue components can be placed in a sterile transport solution after aseptic recovery. The sterile transport solution is used to provide an advantageous medium to the natural function of the placental tissue components prior to processing. For example, calcium-rich water can be used as the sterile transport solution to provide a medium to drive undifferentiated cells to become osteogenic when implanted. Throughout the preparation of the human birth tissue material, various methods can be used to drive undifferentiated cells to differentiate into specialized cell types including, but not limited to, transport solutions, soaks, particular temperature ranges, and hyperbaric pressure.

The sterile transport solution preferably includes sodium chloride (NaCl) in a concentration range from typically about 10% to typically about 20% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water.

Amniotic fluid can be placed in a sterile container after aseptic recovery. In a preferred embodiment, a cell count is performed on the amniotic fluid using methods commonly known in the art (e.g., hemocytometer). The amniotic fluid is preferably mixed thoroughly before a sample is taken to ensure that the sample is representative of the number of cells dispersed throughout the amniotic fluid. Additionally, an appropriate dilution of the mixture with regard to the number of cells to be counted can be utilized. The total cell count per milliliter can then be calculated. In another embodiment, a cell counter can be used to determine total cell count per milliliter of fluid. After the cell count is determined, a requisite cell suspension solution volume can be calculated and prepared. The cell suspension volume may be calculated from predetermined requirements for the minimum starting gram weight of tissue per mL of bulk tissue product. In an alternate embodiment, the cell suspension volume may be calculated from predetermined requirements for the minimum number of amniotic fluid cells per 1.0 mL aliquot of bulk tissue product. In one embodiment, the cell suspension solution includes typically about 91% volume of Plasma Lyte-A and typically about 9% volume of human albumin 25% solution.

In a preferred embodiment, after the cell count is completed, an amniotic fluid composition is prepared according to the following steps. Particles in the amniotic fluid are separated from the liquid component of the amniotic fluid using centrifugation. The resulting, separated particles are referred to as "pellets." The separation of particles from the liquid component of the amniotic fluid may occur by any art-recognized method including sedimentation or microfiltration. In a preferred embodiment, the amniotic fluid is evenly aliquoted into sterile conical centrifuge tubes. The amniotic fluid can be distributed in equal amounts in as many tubes as necessary for the volume recovered. The amniotic fluid can be centrifuged at 200 rpm to 15,000 rpm for a period of up to 30 minutes at ambient temperature. In one embodiment, the amniotic fluid is centrifuged at approximately 1410 rpm (400×gravity [RCF]) for a period of 10 minutes at ambient temperature. Using a sterile pipette, the supernatant can be aspired from each tube and discarded. An isotonic solution can be used to re-suspend each pellet and bring the volume of each tube up to a predetermined amount. In one embodiment, the isotonic solution is Plasma Lyte-A. The pellet/isotonic solution combination can be centrifuged at 200 rpm to 15,000 rpm for a period of up to 30 minutes at ambient temperature. In one embodiment, the pellet/isotonic solution combination is centrifuged at approximately 1410 rpm (400×g [RCF]) for a period of 10 minutes at ambient temperature. Using a sterile pipette, the second supernatant can be aspired from each tube and discarded. Each second pellet can be re-suspended in a cell suspension solution of a predetermined amount to form the amniotic fluid composition. In one embodiment, the cell suspension solution includes Plasma Lyte-A and human albumin 25% solution. In a preferred embodiment, the cell suspension solution includes typically about 91% volume of Plasma Lyte-A and typically about 9% volume of human albumin 25% solution. The cells in each tube can be thoroughly suspended by using a vortex mixer for a minimum of three seconds. Immediately thereafter, the contents of each tube are homogenized with a cell suspension solution to form the amniotic fluid composition. In a preferred embodiment, the cell suspension solution includes typically about 91% volume of Plasma Lyte-A and typically about 9% volume of human albumin 25% solution.

In one embodiment, the discarded first and second supernatant from the aforementioned amniotic fluid composition preparation steps are further precipitated using dialysis equipment or micropore/nucleopore filters. Alternately, the first and second supernatant can be further precipitated by pipetting the supernatants onto sterile wax paper, heating the contents to quickly evaporate the liquid, and then adding the remaining material back into the final amniotic fluid composition. This method allows for the removal of the extraneous liquid, while maximizing the cells, proteins and other particles otherwise discarded in the first and second supernatants. The remaining material precipitated from the first and second supernatants can be homogenized with the amniotic fluid composition.

After the amniotic fluid composition is generated, a second cell count can be performed on a representative sample using a hemocytometer, a cell counter, or any other method commonly known in the art. The amniotic fluid preparation can be stored at typically about 1-10° C. for a period of up to 24 hours pending further processing.

A predetermined percentage of the amniotic fluid composition (representative sample) can be retained for testing and not included in the final bulk product. This representative sample can be retained for analysis and comparison to the cells in the final bulk product to discern any deleterious effects on the amniotic fluid cells, particularly the effects of the cryoprotectant(s) on the amniotic fluid cells in the final bulk product and/or the effects of cleaning, processing, freezing and thawing on the amniotic fluid cells.

Simultaneous with the initial cell count of the amniotic fluid, the weight of the placental tissue components can be determined. Thereafter, the placental tissue components can be transferred aseptically to a sterile dish containing Plasma Lyte-A and stored in a quarantine refrigerator pending further processing.

After the weight of the placental tissue components is determined, a requisite tissue suspension solution volume can be calculated and prepared based on predetermined requirements for the minimum starting gram weight of tissue per mL of bulk tissue product. In one embodiment, the tissue suspension solution comprises Plasma Lyte-A, human albumin 25% solution, and dimethyl sulfoxide. In a preferred embodiment, the tissue suspension solution comprises: typically about 44% volume of Plasma Lyte-A, typically about 36% volume of human albumin 25% solution, and typically about 20% volume of dimethyl sulfoxide.

In one embodiment, the total number of final product units can be calculated based on predetermined requirements for: (1) the minimum starting tissue gram weight per mL of bulk tissue product; and (2) the minimum number of amniotic fluid cells per 1.0 mL aliquot of bulk tissue product. In a preferred embodiment, the total number of final product units can be calculated based on predetermined requirements for the minimum starting tissue gram weight per mL of bulk tissue product. In one embodiment, the final product vials can be of various volumes such as, for example, 0.25 mL, 0.50 mL, 1.0 mL, 1.25 mL, 2.0 mL, 3.0 mL or any other volume as contemplated by one of ordinary skill in the art.

In one embodiment, the placental tissue components include amniotic membrane. In another embodiment, the placental tissue components include one or more components selected from the group consisting of amniotic membrane, chorionic membrane, Wharton's jelly, umbilical cord tissue, umbilical cord blood, placental globe, and other gelatins, other cells and extracellular matrix from placental tissue components. The placental tissue components can them be placed in a sterile dish containing Plasma Lyte-A until further processing.

The placental tissue components can be removed from the Plasma Lyte-A and cryopreserved according to methods commonly used in the art. The placental tissue components can be soaked in cryoprotectant prior to cryopreservation. In one embodiment, the cryoprotectant is one commonly used in the industry, such as, for example, dimethyl sulfoxide (DMSO). In a preferred embodiment, the cryoprotectant is an amnion control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. Any cryoprotectant specific to the birth tissue material described herein may be used. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

After cryopreservation, the placental tissue components are subjected to morselization. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used. In one embodiment, the total number of final product units can be calculated based on predetermined requirements for: (1) the minimum tissue gram weight after morselization per mL of bulk tissue product; and (2) the minimum number of amniotic fluid cells per 1.0 mL aliquot of bulk tissue product. In an alternate embodiment, the total number of final product units can be calculated based on predetermined requirements for the minimum tissue gram weight after morselization per mL of bulk tissue product.

After morselization, the milled placental tissue components can be combined with the tissue suspension solution to form a tissue suspension. In one embodiment, the tissue suspension solution includes Plasma Lyte-A, human albumin 25% solution, and dimethyl sulfoxide, which is used immediately to prepare the final bulk tissue product. In a preferred embodiment, the tissue suspension solution comprises typically about 44% volume of Plasma Lyte-A, typically about 36% volume of human albumin 25% solution, and typically about 20% volume of dimethyl sulfoxide, which is used immediately to prepare the final bulk tissue product. In an alternate embodiment, the tissue suspension solution includes typically about 44% volume of Plasma Lyte-A and typically about 36% volume of human albumin 25% solution. The 20% volume of dimethyl sulfoxide is purposefully withheld pending final combination of the bulk tissue product. In this alternate embodiment, the milled tissue suspension (without dimethyl sulfoxide) can be stored at about 1-10° C. for a period of up to about 24 hours, pending further processing. In the alternate embodiment, the 20% volume of dimethyl sulfoxide can be added to the tissue suspension immediately prior to final bulk tissue product manufacture.

Bulk tissue product can be manufactured by homogenizing the amniotic fluid composition and the tissue suspension. Both the amniotic fluid composition and the tissue suspension can be vortexed for no less than about three seconds prior to combination. In a preferred embodiment, the bulk tissue product can be homogenized using a laboratory homogenizer mixer, followed by continuous mixing with magnetic stirrers. Immediately thereafter, the bulk tissue product can be placed on cold packs and individual, empty cryovials can be filled with the bulk tissue product. In one embodiment, the final product vials can be of various volumes such as, for example, 0.25 mL, 0.50 mL, 1.0 mL, 1.25 mL, 2.0 mL, 3.0 mL or any other volume as contemplated by one of ordinary skill in the art. Cryopreservation of the final bulk tissue product vials can be achieved through control-rate freezing by methods commonly known in the art.

Representative samples from the beginning, middle, and end of the cryovial fill cycle can be removed from the final product count for quality control testing, including, but not limited to, bioburden testing, mycoplasma DNA by polymerase chain reaction, and bacterial endotoxin test (Limulus Ameboycte Lysate). Representative samples from the beginning, middle, and end of the cryovial fill cycle can be removed from the final product count to store for future testing should the need arise.

Another embodiment of a method for preparing a birth tissue material composition is provided herein. According to one embodiment, the composition includes human placental tissue components. The composition can optionally include an acceptable carrier composition. The human placental tissue components can be prepared according to the steps provided herein. In certain embodiments, the human placental tissue components can be combined with the carrier composition to formulate a composition suitable for application on or within an affected site of a body.

To prepare the human placental tissue components for inclusion in a composition, placental tissue components are initially recovered from a seronegative, healthy woman per the aforementioned donor screening procedures, including a comprehensive medical history and behavior risk assessment, physical exam and infectious disease testing.

Placental tissue is preferably recovered from a full-term Cesarean delivery of a newborn. Alternatively, placental tissue is recovered from a full-term vaginal delivery of a newborn. The subsequent steps of preparing the placental tissue components are performed in a controlled environment (i.e., certified biological safety cabinet, hood or clean room). Instruments, solutions, and supplies coming into contact with the human placental tissue material during processing are sterile. All surfaces coming in contact with the human placental tissue material intended for transplant are either sterile or draped using aseptic technique.

According to one embodiment, the human placental tissue components can include one or more components selected from the group consisting of amniotic membrane, chorionic membrane, Wharton's jelly, umbilical cord tissue, umbilical cord blood, placental globe, and other gelatins, other cells and extracellular matrix from placental tissue. Other variations of the invention include, however, removing one or more of the amniotic membrane, chorionic membrane, Wharton's jelly, umbilical cord tissue, umbilical cord blood, placental globe, and other gelatins, other cells and extracellular matrix from placental tissue before further processing. In a preferred embodiment, the placental tissue components include amniotic membrane only. Removal of one or more of the placental tissue components can be achieved via a sterile saline solution rinse, blunt dissection, scalpel, or a combination thereof, if necessary.

The retained placental tissue components can be placed in a sterile transport solution after aseptic recovery. The sterile transport solution is used to provide an advantageous medium to the natural function of the placental tissue components prior to processing. Throughout the preparation of the human placental tissue composition, various methods can be used to drive undifferentiated cells to differentiate into specialized cell types including, but not limited to, transport solutions, soaks, particular temperature ranges, and hyperbaric pressure.

The sterile transport solution preferably includes sodium chloride (NaCl) in a concentration range from typically about 0.9% to typically about 20% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water.

After delivery to the processing facility, the weight of the placental tissue components can be determined. Thereafter, the placental tissue components can be transferred aseptically to a sterile dish containing Plasma Lyte-A and stored in a quarantine refrigerator pending further processing.

The placental tissue components can be removed from the Plasma Lyte-A and cryopreserved according to methods commonly used in the art. The placental tissue components can be soaked in cryoprotectant prior to cryopreservation. Various cyroprotectants are often used to avoid the formation of ice crystals and/or delay the onset of ice formation to the lowest temperature possible. Such cryoprotectants known in the art are typically glycerol, dimethyl sulfoxide (DMSO), dimethyl acetamide, methanol, ethylene glycol, propylene glycol, trimethylamine acetate, and other high molecular weight solutes capable of forming strong hydrogen bonds to water, which may be used singularly or in combination thereof. In one embodiment, the cryoprotectant is dimethyl sulfoxide (DMSO) at a concentration of about 10% (v/v). In a preferred embodiment, the cryoprotectant is an amnion control rate freeze solution comprising Plasma Lyte-A, human albumin 25% solution, and dimethyl sulfoxide. In another embodiment, the cryoprotectant is a commercially available cryoprotectant such as Synth-a-Freeze® available from Invitrogen. However, any cryoprotectant specific to the placental tissue components described herein may be used. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

According to one embodiment, after cryopreservation, the placental tissue components are subjected to morselization. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used.

After morselization, the milled placental tissue components can be homogenized with a tissue suspension solution to form the final product. In one embodiment, the tissue suspension solution includes Plasma Lyte-A, human albumin 25% solution, and dimethyl sulfoxide. In a preferred embodiment, the tissue suspension solution comprises typically about 67.5% volume of Plasma Lyte-A, typically about 22.5% volume of human albumin 25% solution, and typically about 10% volume of dimethyl sulfoxide. In another embodiment, the tissue suspension solution comprises typically about 0.01%-10% volume of dimethyl sulfoxide combined with a medium or buffer, including, but not limited to, sodium chloride, glycerol, methylcellulose or appropriate buffer solutions, e.g., phosphate buffered saline.

Final product can be manufactured by homogenizing the placental tissue components and the tissue suspension solution. In a preferred embodiment, the final product can be homogenized using a laboratory homogenizer mixer, followed by continuous mixing with magnetic stirrers. Immediately thereafter, the final product can be placed on cold packs and aliquoted into individual, empty cryovials. In one embodiment, the final product can be of various volumes such as, for example, 0.25 mL, 0.50 mL, 1.0 mL, 1.25 mL, 2.0 mL, 3.0 mL or any other volume as contemplated by one of ordinary skill in the art. Cryopreservation of the final bulk tissue product vials can be achieved through control-rate freezing by methods commonly known in the art.

Representative samples from the beginning, middle, and end of the cryovial fill cycle can be removed from the final product count for quality control testing, including, but not limited to, bioburden testing, mycoplasma DNA by polymerase chain reaction, and bacterial endotoxin test (Limulus Ameboycte Lysate). Representative samples from the beginning, middle, and end of the cryovial fill cycle can be removed from the final product count to store for future testing should the need arise.

In one embodiment, the total number of final product units can be calculated based on predetermined requirements for the minimum starting tissue gram weight per mL of final product. In an alternate embodiment, the total number of final product units can be calculated based on predetermined requirements for the minimum tissue gram weight after morselization per mL of final product.

Another embodiment of a method for preparing a birth tissue material composition is provided herein. According to one embodiment, the composition includes human placental tissue components. In some aspects, the placental tissue components may be subjected to morselization following recovery. As used herein, "morselization" means to grind up to particle form. Tissue morselization may occur by any art-recognized method of tissue disruption, including, but not limited to, milling, blending, sonicating, homogenizing, micronizing, pressing, pulverizing, triturating, macerating, or a combination thereof. Particles may be micron or sub-micron size. The resulting product may be a dry powder. In some embodiments, the morselized placental tissue components are dissolved in one or more biocompatible solvents to create a paste, emulsion, suspension or solution. This dissolution may occur during the manufacturing process or immediately prior to application. Examples of biocompatible solvents include, but are not limited to, physiological saline; BSS™, a balanced salt solution containing per ml 0.64% sodium chloride, 0.075% potassium chloride, 0.048% calcium chloride, 0.03% magnesium chloride, 0.39% sodium acetate, and 0.17% sodium citrate dihydrate, as well as sodium hydroxide and/or hydrochloric acid to adjust pH, and water; Ocular Irrigation Solution™; Lactated Ringer's solution; normal saline solution; or normal saline adjusted to pH 7.4 with sodium bicarbonate.

In some embodiments, the placental tissue components are morselized by use of a tissue grinder (e.g., a Potter-Elvehjem grinder or a Wheaton Overhead Stirrer). In some embodiments, the placental tissue components are micronized by use of a sonicator. In some embodiments, the placental tissue components are micronized by use of a bead beater. In some embodiments, the placental tissue components are micronized by use of a freezer/mill (e.g., a SPEX SamplePrep Freezer/Mill). In some embodiments, the placental tissue components are micronized by manual use of a pestle and mortar. The placental tissue components may be optionally lyophilized before or after being subjected to micronization.

The human birth tissue material compositions as described herein can be optionally mixed with bioactive agents such as physiologically compatible minerals, growth factors, wound healing agents (e.g., cytokines including but not limited to PDGF, TGF, and thymosin), hyaluronic acid, wound sealants (such as fibrin with or without thrombin), cellular attractant and scaffolding reagents (e.g., fibronectin) antibiotics, chemotherapeutic agents, antigens, antibodies, enzymes, vectors for gene delivery and hormones.

The human birth tissue compositions as described herein can be optionally mixed with a suitable carrier to form a composition suitable for treatment of inflammation, pain or both inflammation and pain on or within an affected site of the body. According to one embodiment, the carrier composition includes one or more vitamins, minerals, proteins, fats, collagens (including collagen extracted from the placental globe), hyaluronic acid, waxes, glycols and derivatives thereof, glyercols and derivatives thereof, oils (including essential oils), fatty acids, cholesterols, alcohols, emollients, adsorbents, lubricants, emulsifying agents, thickening agents, humectants, surfactants, pharmaceutical ingredients, preservatives, antifungal agents, antioxidants, antimicrobial agents, structuring agents, dispersing agents, pH-adjusting components, sequestering or chelating agents, wetting agents, coloring agents, and other components known in the art to be suitable for use in a composition that can be applied onto or within the human body. The optional carrier composition can be formulated in such a way that the combination of the human birth tissue material composition and the carrier composition are chemically compatible and do not form complexes which precipitate from the final composition.

According to one embodiment, the human birth tissue material composition and the carrier composition as provided herein can be mixed or blended according to a variety of conventional techniques. According to one embodiment, the human birth tissue material composition and the carrier composition can be mixed in a manner to produce a smooth and homogenous composition. According to one embodiment, the human birth tissue material composition as provided herein is introduced to the carrier composition after the carrier composition is formed (i.e., post-added). In an alternative embodiment, the human birth tissue material composition is introduced during carrier composition preparation. The amount of placental tissue present in the composition can vary depending upon whether a carrier composition is utilized, the frequency of use, and the treatment desired. The amount of carrier composition present in the final composition can vary according to the final formulation of the composition. According to one embodiment, the carrier composition components can be present in an amount from typically about 0.1% to about 99.0% based on total composition weight.

According to one embodiment, the methods of the present invention include the treatment of inflammation, pain, or both inflammation and pain arising from inflammatory diseases or conditions within a body. In certain embodiments, the disease or condition is an inflammatory disease of the skin or the mucosal membrane including, but not limited to, eczema, psoriasis, acne, seborrhea, seborrheic dermatitis, ichthyosis, ulcers, psoriasis, seborrheic dermatitis of the face and trunk, seborrheic blepharitis, contact dermatitis, stasis dermatitis and exfoliative dermatitis. In other embodiments, the inflammatory disease or condition is an ocular condition, including, but not limited to, conjunctivitis, uveitis, anterior uveitis, glaucoma, scleritis and dry eye syndrome. In other embodiments, the inflammatory disease or condition is a rheumatic disease, including, but not limited to, osteoarthritis, rheumatoid arthritis, juvenile rheumatoid arthritis, fibromyalgia, scleroderma, spondyloarthropathies, gout, infectious arthritis, polymyalgia rheumatica, polymyositis, psoriatic arthritis, bursitis, tendinitis, CIAS1-related Autoinflammatory Periodic Syndromes (CAPS), pelvic inflammatory disease, interstitial cystitis or Henoh-Schonlein purpura. In other embodiments, the inflammatory disease or condition is an inflammatory disorder, including, but not limited to, autoimmune diseases (e.g., systemic lupus erythematosus, Sjogren's syndrome, sarcoidosis, Behcet's syndrome, ankylosing spondylitis, haemolytic autoimmune anaemias, multiple sclerosis and amyotrophic lateral sclerosis), amyloidosis, asthma, atherosclerosis, osteoporosis, bronchitis, enuresis, eosinophilic disease, gastrointestinal disorders (e.g., Inflammatory Bowel Disease, peptic ulcers, regional enteritis, diverticulitis, gastrointestinal bleeding, Crohn's disease, gastritis, diarrhea, irritable bowel syndrome and ulcerative colitis), gastroesophageal reflux disease, eosinophilic esophagitis, gastroparesis such as diabetic gastroparesis, food intolerances and food allergies.

The methods of the present invention can also be used to treat inflammation associated with conditions, including, but not limited to, vascular diseases, migraine headaches, tension headaches, periarteritis nodosa, thyroiditis, aplastic anemia, Hodgkin's disease, scierodoma, rheumatic fever, type I diabetes, myasthenia gravis, nephrotic syndrome, polymyositis, gingivitis, hypersensitivity, conjunctivitis, multiple sclerosis, and ischemia (e.g., myocardial ischemia). The compounds may be useful for treating neuroinflammation associated with brain disorders (e.g., Parkinson's disease and Alzheimer's disease) and chronic inflammation associated with cranial radiation injury. The compounds may be useful for treating acute inflammatory conditions (such as those resulting from infection) and chronic inflammatory conditions (such as those resulting from asthma, arthritis and inflammatory bowel disease). The compounds may also be useful in treating inflammation associated with trauma and non-inflammatory myalgia.

According to one embodiment, the methods of the present invention include the treatment of inflammation, pain, or both inflammation and pain arising from a viral infection on or within a body. Examples of viruses giving rise to inflammation, pain, or both inflammation and pain within a body include, but are not limited to, viruses of the Herpesviridae family (e.g., herpes simplex virus-1, herpes simplex virus-2, varicella zoster (shingles), Epstein-Barr virus, cytomegalovirus, roseolovirus, pityriasis rosea and Kaposi's sarcoma-associated herpesvirus), viruses of the Poxviridae family (e.g., Molluscum contagiosum virus), human lymphotrophic viruses (e.g., HTLV-1 and HTLV-2), human immunodeficiency viruses (e.g., HIV-1 and HIV-2) and any other virus that may rest latent within the body of a human or animal and later activate in response to external stimuli.

According to preferred embodiment, the method includes the treatment of inflammation, pain, or both inflammation and pain arising on or within the skin or mucosal membranes. Such inflammation and pain may manifest in the form of blisters or lesions of the dermis or epidermis and mucosal membranes. For example, such manifestations include canker sores, cold sores, fever blisters and genital lesions. In certain embodiments, inflammation and pain may manifest in the form of pressure, itch, tickle, tingle, sensitization, or numbness. Such symptoms can arise when a virus is situated in the neuronal tissue (e.g., nerve cell bodies in the ganglia). Alternatively, such symptoms may be related to diseases or conditions such as atopy, diabetes, multiple sclerosis, and hypertension. Thus, the methods provided herein are particularly suited for treatment of neurogenic inflammation. By treating neurogenic inflammation, the onset of neuropathic pain is ultimately prevented.

According to one embodiment, the methods of the present invention include the treatment of pain wherein said pain is neuropathic pain. In a specific embodiment, the neuropathic pain is caused by a virus, e.g., varicella zoster, herpes (e.g., herpes simplex) or human immunodeficiency virus (HIV). In a specific embodiment, said neuropathic pain is caused by diabetic neuropathy. In another specific embodiment, said neuropathic pain is caused by injury to a nerve in said individual. In another specific embodiment, said neuropathic pain is caused by a drug. In certain specific embodiments, said drug is or comprises a platinum-containing anticancer drug, e.g., oxaliplatin, carboplatin or cisplatin, or another chemotherapeutic drug such as paclitaxel or vincristine. In another embodiment the pain is cause by radiation injury, e.g., radiation injury that is part of cancer treatment. In another specific embodiment, said neuropathic pain is caused by inflammation, e.g., neuroinflammation, neuritis.

According to another embodiment, the methods of the present invention include the treatment of pain wherein said pain is inflammatory pain. In another embodiment, said pain is bone pain. In a specific embodiment, said bone pain is associated with or caused by cancer. In another embodiment, said pain is unresponsive to steroid therapy. In another embodiment, said pain is unresponsive to non-steroidal anti-inflammatory therapy. In another embodiment, said pain is unresponsive to opioid therapy. In another embodiment, said pain is unresponsive to opiate therapy.

According to another embodiment, the human birth tissue material composition is used to treat inflammation and/or pain associated with muscle conditions such as inflammatory myopathies (e.g., myositis, dermatomyositis, inclusion body myositis, polymyositis) and myofascial pain syndrome (e.g., trigger points).

According to one embodiment, the human birth tissue material composition described herein may be administered by a user (i.e., medical professional) either through injection or by direct application to the chosen site. Modes of administration include, but are not limited to: intramuscular, subcutaneous, intraperitoneal, percutaneous, soft tissue injection, intravenous, intravascular, intracerebral, transdermal, intraocular, topical or mucosal. A single injection or multiple injections may be administered which can be to a single site or to more than one site in the subject to be treated. Multiple administrations may occur essentially at the same time or separated in time. Suitable formulations may include, but are not limited to, a cream, emulsion, spray, gel, ointment, salve, butter, gel, putty, balm, or pliable stick. In one embodiment, the gel or putty carrier could be achieved through collagen extracted from the placental globe.

In another aspect of the present invention, the human birth tissue material composition described herein can be used alone, or in combination with one or more additional structural carriers, including, but not limited to, a placental membrane construct (e.g., amniotic membrane wound covering), a soft tissue allograft, a bone allograft (e.g., FDBA), or platelet rich plasma. The human birth tissue material composition can be used alone, or in combination with one or more additional bioactive agents such as physiologically compatible minerals, growth factors, antibiotics, chemotherapeutic agents, antigen, antibodies, enzymes, vectors for gene delivery and hormones.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

Example 1

The placental construct may be prepared according to the method of FIG. 1, the details of which are herein provided.

Human birth tissue was obtained from a seronegative, healthy mother via Cesarean section. To maximize the overall quality of the donated tissue, a recovery technician was present in the operating room during the donor's Cesarean section to assist the surgical team with recovery, treatment and handling of the birth tissue. The donor was surgically prepped and draped per AORN standards prior to the Cesarean section procedure. The recovery technician prepared the recovery site by establishing a sterile field on a back table in the operating room.

Amniotic fluid was recovered according to the following procedures provided herein. The physician's assistant cleared all maternal blood from the surgical site. A suction cannula was positioned directly above the intended amnion/chorion membrane incision site. Using the smallest appropriate incision, the amniotic and chorionic membranes were breached, releasing the amniotic fluid into the suction cannula. Avoiding maternal blood, the physician's assistant suctioned as much amniotic fluid volume as possible into a sterile suction canister. Immediately following recovery, the sterile suction canister was transferred to the sterile back table. The recovery technician examined the amniotic fluid for the presence of visible blood. After noting that no visible blood was present, the recovery technician aseptically transferred the amniotic fluid to a sterile Nalgene jar and performed swab cultures. The recovery technician secured the lid on the Nalgene jar to which the appropriate identification was affixed.

Following delivery of the baby, the physician's assistant placed the human birth tissue en-bloc into a sterile basin. Maintaining sterility, the basin was transferred to the recovery technician onto the sterile field on the back table. Beginning at the amnion/chorion membrane surgical incision site, the recovery technician used blunt dissection to separate the chorionic membrane from the amniotic membrane, using care not to tear the amniotic membrane. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 mL of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed.

The Nalgene jar containing the amniotic fluid and the plastic transport container containing the amniotic membrane were placed in a qualified shipping container with an appropriate amount of wet ice to maintain refrigerated temperatures. The validated box arrived at the processing facility approximately one hour following recovery and was immediately inspected per standard operating procedures and placed in refrigerated temperatures (1-10° C.).

Processing was performed on a sterile field using aseptic technique in a validated cleanroom at the processing facility less than four hours after the recovery was completed. All manufacturing steps were recorded concurrently by a circulating technician on a designated processing record.

Amniotic Membrane Preparation

The amniotic membrane was removed from the plastic transport container and outer bag. The inner bag containing the amniotic membrane was aseptically passed onto a sterile field. Approximately 35 mL of the sterile transport solution was aspirated out of the bag utilizing a sterile pipette. Subsequently, the sample was transferred to a sterile conical tube for pre-processing bioburden testing. Using sterile forceps, the amniotic membrane was removed from the inner bag and placed in a sterile basin on a sterilely draped pre-set balance. The weight of the amniotic membrane was recorded. The sterile basin containing the amniotic membrane was transferred to a back table. Approximately 250 mL of Plasma Lyte-A was added to a second sterile basin and covered with the corresponding sterile lid. Using sterile forceps, the amniotic membrane was removed from the first sterile basin and transferred to a sterile prep board where the membrane was spread flat. Using a sterile lap sponge, any remaining debris/blood was removed from the surface of both sides of the amniotic membrane. The amniotic membrane was subsequently transferred to a second sterile basin containing Plasma Lyte-A where the membrane was covered, labeled and transferred to a quarantine refrigerator.

Amniotic Fluid Preparation

Sterile pipettes and 50 mL sterile conical centrifuge tubes were transferred to a sterile field. The Nalgene jar was moved in a gentle swirling motion to ensure cells were equally dispersed throughout amniotic fluid prior to removal of samples. The Nalgene jar containing the amniotic fluid was opened, and 10 mL of amniotic fluid was aspirated out utilizing a sterile pipette and transferred to a sterile conical tube for pre-processing bioburden testing. Approximately one mL of amniotic fluid was aspirated out utilizing a sterile pipette in order to complete the cell count. Utilizing a sterile 50 mL pipette, the remaining amniotic fluid was aseptically aspirated out of the Nalgene jar and transferred into 50 mL conical centrifuge tubes. Aliquots of the amniotic fluid were aseptically distributed in equal amounts in an even number of 50 mL sterile conical centrifuge tubes.

Batch Volume and Aliquot Fill Calculation

The batch volume and aliquot fill calculations (See FIG. 2) were determined based on the following calculations.
1. Record Amnion Weight (AW) in grams.
2. Calculate Amnion Allowable Aliquots (AA).
   2.1 Divide Amnion Weight (AW) by minimum starting amnion gram weight per 1 mL aliquot (0.03 grams) to calculate total Amnion Allowable Aliquots (AA).
3. Calculate Cell Count
   3.1 Record the total Amniotic Fluid Volume (A) in mL.
   3.2 Record the Total Cells Counted (B) for the four large corner squares and the middle square of the hemocytometer counting grid using the hemocytometer and an inversion microscope per standard operating procedures.
   3.3 Calculate Average Cells/Square (C).
      3.3.1 (C)=Total Cells Counted (B)/5 Squares Counted
   3.4 Record Dilution Factor used in preparation of cell count (D).
   3.5 Calculate the Total Cell Density (cells/mL) (E).
      3.5.1 (E)=(C)×(D)×$10^4$
   3.6 Calculate Total Cells (TC).
      3.6.1 Total Cells (TC)=Total Cell Density (E)×Total Volume of Amniotic Fluid (A)
4. Calculate Aliquot Cell Density (CD) (Aliquot=1 mL).
   4.1 (CD)_mL=Total Cell (TC)/Amnion Allowable Aliquot (AA)
5. Determine Bulk Product Volume (BV).
   5.1 (AA) Amnion Allowable Aliquots=Bulk Product Volume (BV)
6. Determine Lot Vial Fill Calculations.
   6.1 Record Bulk Product Volume (BV)
   6.2 Record the target vial production per size provided by management.
   6.3 Calculate Total Vial Target
   6.4 Calculate Total Volume Requirement for Vial Target.
      6.4.1 [Vial Target for 0.25 mL vials]×0.25=Volume Requirement (mL) for 0.25 mL Vials
      6.4.2 [Vial Target for 0.50 mL vials]×0.50=Volume Requirement (mL) for 0.5 mL Vials
      6.4.3 [Vial Target for 1.25 mL vials]×1.25=Volume Requirement (mL) for 1.25 mL Vials
   6.5 Calculate Total Vial Fill Volume.
   6.6 Compare Bulk Product Volume to Total Vial Fill Volume requirement based on the production plan.
      6.6.1 Total Vial Fill Volume must be Bulk Product Volume (BV).
      6.6.2 Adjust vial targets accordingly.

Solutions Calculations

After obtaining the Bulk Product Volume (BV), the component volumes for the tissue suspension solution (i.e., amnion suspension solution) and the cell suspension solution were determined based on the following calculations (See FIG. 3).
1.0 Bulk Product Volume (mL) (BV)=Total Suspension Solution Volume (mL) (SS)
2.0 Calculate Cell Suspension Solution Volume (CS)
   2.1 (CS)=Total Suspension Solution Volume (SS)/2
   2.2 Calculate (CS) Component Volume(s) Required:
      2.2.1 Plasma Lyte-A Volume (mL)=(CS)×0.91
      2.2.2 Human Albumin 25% Solution Volume (mL)=(CS)×0.09
   2.3 Calculate Amnion Suspension Solution (AS)
      2.3.1 (AS)=Total Suspension Solution Volume (SS)/2
      2.3.2 Calculate (AS) Component Volume(s) Required:
         2.3.2.1 Plasma Lyte-A Volume (mL)=(AS)×0.44
         2.3.2.2 Human Albumin 25% Sol. Volume (mL)=(AS)×0.36
         2.3.2.3 Dimethyl Sulfoxide, USP Volume (mL)=(AS)×0.20

Solution Preparations

The following materials were transferred to the sterile field: (i) Human Albumin 25% Solution, Excipient, EU Grade; (ii) Plasma Lyte-A Injection (pH 7.4); and (iii) DMSO (dimethyl sulfoxide), USP. In separate 1 L sterile containers, the cell suspension solution and the amnion suspension solution were prepared based on the calculations obtained utilizing the solution calculations sheet set forth in FIG. 3. The amnion control rate freeze solution was prepared according to the directions as set forth in FIG. 3. The containers were labeled with respective solution names, lot numbers, and expiration dates and stored at 1-10° C. pending further use.

Aseptic Processing of Amniotic Fluid Composition

Amniotic fluid-filled conical tubes were aseptically transferred to an Eppendorf centrifuge and centrifuged at 400×g for 10 minutes at ambient temperature. At the completion of each cycle, the conical tubes were aseptically transferred back to the sterile field. Each conical centrifuge tube was checked by a processing technician to ensure a pellet had formed. The results were recorded in the batch record. The supernatant was removed and discarded using a sterile pipette, and a sufficient volume of Plasma Lyte-A was added to each conical tube to re-suspend the pellet and increase the volume in each tube to approximately 20 mL. Each tube was placed on a vortex mixer for 3-5 seconds to fully re-suspend the pellets. The contents of the conical centrifuge tubes were subsequently combined, reducing the overall conical centrifuge tube number by half by quickly pouring the suspension from a first tube to a second tube, ensuring maximum transfer of cells during combination. The process was repeated until all remaining conical centrifuge tubes were combined, reducing the number of tubes by half. The remaining conical centrifuge tubes were aseptically transferred to an Eppendorf centrifuge and centrifuged at 400×g for 10 minutes at ambient temperature. At the completion of each cycle, the conical tubes were aseptically transferred back to the sterile field. Each conical centrifuge tube was checked by a processing technician to ensure a pellet had formed. The results were recorded in the batch record. The supernatant was removed and discarded using a sterile pipette, and a sufficient volume of cell suspension solution was added to each conical tube to re-suspend the pellet and increase the volume in each tube to approximately 20 mL. Each tube was placed on a vortex mixer for 3-5 seconds to fully re-suspend the pellets. Next, each suspension was quickly poured into the container of cell suspension solution to form the amniotic fluid composition. The amniotic fluid composition was stored in refrigerated temperatures at 1-10° C. until further processing.

Amnion Control Rate Freezing

The following materials were transferred to the sterile field: amnion (in Plasma Lyte-A solution); amnion control rate freeze solution; appropriately sized pipettes; sterile bowl; sterile forceps, sterile tray; and sterile spatula. The amnion was removed from Plasma Lyte-A solution and transferred to the amnion control rate freeze solution. After 30 minutes, the amnion was removed from the amnion control rate freeze solution and transferred to the sterile tray where it was cut into four equal sections. The tray with the sectioned amnion was aseptically transferred to a control rate freezer. A control rate freezer probe was placed near the center of the chamber, taking care not to contact any metal in the chamber. The control rate freezer was activated by selecting a pre-programmed cycle.

Amnion Morselization

The amnion was subjected to morselization by cryogenic milling by the procedures described herein. A Spex Freezer/Mill® was programmed to the following settings: grinding rate=12; cycles=3; pre-cooling time=5 minutes; grinding time=2 minutes; and intermediate cooling=2 minutes. Sterile, autoclaved milling cylinders, impactors and end-caps were placed in an ultra-low freezer for a minimum of 15 minutes in order to pre-cool the materials prior to use. The milling cylinders, impactor and end-caps were removed from ultra-low freezer and aseptically transferred to the sterile field. One end cap was inserted onto each cylinder. The amnion was subsequently removed from the control rate freezer. One amnion section was placed into each of the four cylinders. An impactor bar was placed inside each of the four cylinders. The second end-cap was secured onto each cylinder, sealing the four milling chambers. The milling chambers were placed into the Spex Freezer/Mill® one at a time and allowed to run for the aforementioned program settings. At the conclusion of each milling event, the chamber was removed and immediately aseptically transferred to a sterile field. Using a sterile extractor tool, an end cap was removed from each chamber. The impactor bar and milled amnion were quickly dispensed into a sterile bowl. A sterile spatula was used to remove any remaining milled amnion from the milling cylinder or end-caps. Approximately 100 mL of amnion suspension solution was added to the milled amnion in a sterile bowl. Once thawed, any remaining amnion was removed from the impactor using a sterile spatula. This milling procedure was repeated for each of the four milling chambers until all milled amnion was added to the amnion suspension solution, thereby forming the tissue suspension.

Bulk Tissue Product

A sterile 2 L Erlenmeyer flask was aseptically transferred to a back table. The tissue suspension (amnion suspended in the amnion suspension solution) and the amniotic fluid composition were aseptically poured into the 2 L Erlenmeyer flask. The flask was appropriately covered and labeled. Immediately thereafter, the flask was placed in a quarantine refrigerator at 1-10° C.

Vial Fill

The following materials were transferred to the sterile field: sterile pipettes; sterile cryovial racks; sterile cryovials; and bulk tissue product. The bulk tissue product was removed from the quarantine refrigerator and placed on cold packs on a sterilely draped mixer. A stir bar was aseptically added to the bulk tissue product. The cryovials were filled using a repeater pipette pre-set to target fill volume as indicated in the production plan. Immediately following fill and capping, each cryovial was inspected per quality control (QC) standard operating procedures. Any vials failing QC inspection were discarded per biohazard waste disposal standard operating procedures. The cryovials that passed QC inspection were placed in cryovial racks.

Bulk Tissue Product Cryopreservation

The cryovial racks were transferred to sterile racks and placed in a control rate freezer. A control rate freezer probe was placed near the center of the chamber, taking care not to contact any metal in the chamber. The control rate freezer was activated by selecting a pre-programmed cycle. Upon completion of each control rate freeze, each cryovial was inspected per QC standard operating procedures. Any vials failing QC inspection were discarded per biohazard waste disposal standard operating procedures. The cryovial racks were placed in sterile containers and transferred to a quarantine ultra-low freezer to await results of all lot release testing before final packaging. Representative samples from the beginning, middle, and end of the cryovial fill cycle were removed from the final product count for lot release testing, which included: bioburden testing, mycoplasma DNA by polymerase chain reaction, and bacterial endotoxin test (Limulus Ameboycte Lysate).

Packaging of Cryopreserved Bulk Tissue Product

Throughout packaging procedures, the cryovials containing bulk tissue product were exposed to ambient temperature for a time period of one minute or less. After lot release testing clearance, each cryovial was packaged into a sterile foil pouch using aseptic technique. Using an AccuSeal 540Plus sealer, each foil pouch was sealed following standard operating procedures. Following QC inspection, each pouch was packaged in an outer box and labeled with the unique tissue identification number assigned to the cryovial, which was designed to ensure the traceability of the tissue from receipt through clinical use, transfer or destruction. Each cryovial was stored at ultra-low temperatures (≤−65° C.) prior to transplantation. Final product vial sizes were 0.25 mL, 0.50 mL, 1.0 mL, 1.25 mL, 2.0 mL and 3.0 mL.

Example 2

Analysis of the human birth tissue material composition prepared substantially according to the methods of Example 1 identified the presence of cytokines associated with immune regulation (ENA-78 [CXCL 5] and ICAM-2). The presence of such cytokines in the human birth tissue material composition may aid in the treatment of inflammation, pain, or both inflammation and pain arising from inflammatory diseases or conditions within a body.

Relative cytokine levels were determined using a sandwich immunoassay array from RayBiotech, Inc. (Human Cytokine Antibody Array C Series 1000, Inc, GA, USA). Before analysis, all samples were homogenized on ice 3×15 seconds with 30 seconds of pause between each step to prevent sample heating and maintain the sample at 4° C. Chemilumenescence was detected using a Foto/Analyst Luminaryfx Workstation (Fotodyne Incorporated, WI, USA), and the signal intensities were measured using TotalLab 100 software (Nonlinear Dynamics, Ltd, UK). Intensity values measured in blank wells were subtracted from all wells, and the data was normalized to a linear curve determined by setting 0% intensity values equal to negative control measurements and 100% intensity values equal to positive control measurements. Final chemokine measurements were given as percent intensity.

Immune-related cytokines were detected including, ENA-78 (CXCL 5), and ICAM-2. ENA-78 was detected at 13.44% (standard deviation=4.20) normalized chemilumenescent intensity, and ICAM-2 was detected at 9.98% (standard deviation=0.86) normalized chemilumenescent intensity. The immunoreductive properties of the human birth tissue material composition may be strongly related to the presence of ENA-78 and ICAM-2. ENA-78 has been found to reduce sensitivity to pain and is produced following the simulation of cells with inflammatory cytokines IL-1 and TNF-α (Dawes, J. M. et al. CXCL5 mediates UVB irradiation—induced pain. *Science translational medicine* 3, 90ra60 (2011)). I-CAM 2 has been shown to mediate interactions important for antigen-specific immune responses, NK-cell mediated clearance, lymphocyte recirculation, and other cellular interactions important for immune responses (NCBI, Vol. 2013 (NCBI, Bethesda, Md.: 2013)).

I claim:

1. A method of treating inflammation, pain or both inflammation and pain in the body of a subject in need thereof, the method comprising the step of:
    administering an effective amount of a human birth tissue material composition on or within the body of the subject,
    wherein the human birth tissue material composition comprises one or more morselized components of a placental organ homogenized with a tissue suspension solution and an amniotic fluid composition, and
    wherein the tissue suspension solution comprises sodium chloride, sodium gluconate, sodium acetate, potassium chloride, magnesium chloride, human albumin 25% solution, and dimethyl sulfoxide.

2. The method of claim 1, wherein the inflammation, pain or both inflammation and pain are located in or on neuronal tissue.

3. The method of claim 1, wherein the pain is neuropathic pain.

4. The method of claim 3, wherein the neuropathic pain is caused by human immunodeficiency virus (HIV) or diabetes.

5. The method of claim 1, wherein the step of administering the human birth tissue material composition includes injecting the composition into the body of the subject.

6. The method of claim 1, wherein the step of administering the human birth tissue material composition includes topical administration to the body of the subject.

7. The method of claim 1, wherein the one or more of the morselized components of the placental organ is selected from the group consisting of placental globe, umbilical cord, umbilical cord blood, chorionic membrane, amniotic membrane, and Wharton's jelly.

8. The method of claim 1, wherein the injectable human birth tissue material composition is cryopreserved until prior to administration.

* * * * *